(12) United States Patent
Al-Dehneh et al.

(10) Patent No.: US 6,548,492 B1
(45) Date of Patent: Apr. 15, 2003

(54) PROCESS FOR FORMULATION OF CARBAPENEM ANTIBIOTIC COMPOSITIONS

(75) Inventors: Anthony Al-Dehneh, Elmwood Park, NJ (US); William A. Hunke, Harleysville, PA (US); Kathleen J. Illig, Phoenixville, PA (US); Anand Kanike, Lansdale, PA (US); Hiren Patel, Parsippany, NJ (US); Scott D. Reynolds, Pekiomenville, PA (US); Stelios C. Tsinontides, Ambler, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/698,808

(22) Filed: Oct. 27, 2000

Related U.S. Application Data

(60) Provisional application No. 60/162,482, filed on Oct. 29, 1999.

(51) Int. Cl.$^7$ .................. C07D 487/04; A61K 31/407; A61P 31/04
(52) U.S. Cl. .................. 514/210.13; 540/350
(58) Field of Search ................. 514/210.13; 540/350

(56) References Cited

U.S. PATENT DOCUMENTS

| | | |
|---|---|---|
| 5,478,820 A | 12/1995 | Betts et al. |
| 5,652,233 A | 7/1997 | Betts et al. |
| 5,952,323 A | 9/1999 | Zimmerman et al. |
| 6,180,783 B1 | 1/2001 | Williams et al. |
| 6,297,231 B1 | 10/2001 | Almarsson et al. |

FOREIGN PATENT DOCUMENTS

| | | |
|---|---|---|
| WO | WO 93/15078 | 8/1993 |
| WO | WO 99/45010 | 9/1999 |

OTHER PUBLICATIONS

Smith, Peter A. S., The Chemistry of Open–Chain Organic Nitrogen Compounds, vol. 1, p. 263, 1965.
Betts et al., Chem. Abs., 118:80721, 1992.

*Primary Examiner*—Mukund J. Shah
*Assistant Examiner*—Thomas C McKenzie
(74) *Attorney, Agent, or Firm*—Sylvia A. Ayler; Valerie J. Camara

(57) ABSTRACT

A novel process for preparing a stabilized, lyophilized carbapenem, antibiotic formulation suitable for intravenous administration to patients in need thereof, wherein the active ingredient is of formula II:

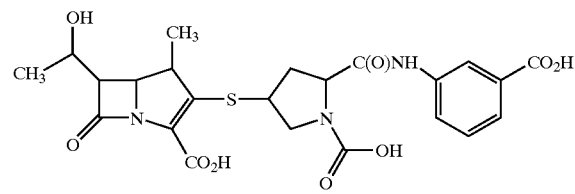

II

The process entails compounding a unstable, monosodium salt carbapenem with a sodium bicarbonate solution at a temperature range of from about 0° to about 5° C. while maintaining a pH between about 7.0 and about 8.0, filtering the resultant solution, bottling under sterile conditions, and lyophilizing to produce the formulation.

22 Claims, 9 Drawing Sheets

PROCESS FOR FORMULATION OF CARBAPENEM ANTIBIOTIC COMPOSITIONS

This application claims the benefit of U.S. Provisional Application No. 60/162,482, filed Oct. 29, 1999.

BACKGROUND OF THE INVENTION

Betalactams, a broader class of antibiotics, further defined as carbapenems useful for the treatment of infectious diseases, including gram positive and negative, aerobic and anaerobic bacteria. U.S. application Nos. 08/926,915 and 09/060,691 to Almarsson et al, filed Sep. 10, 1997, and Apr. 15, 1998, respectively, now assigned to Merck & Co., Inc., teach a novel carbapenem antibiotic compound of formula I:

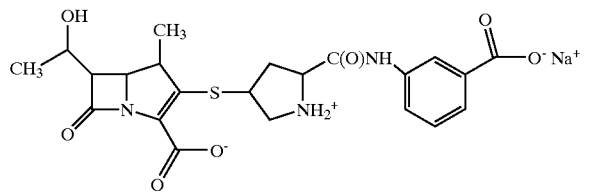

I and a process for the preparation thereof. The compound of formula I, prepared by chemical synthesis, is a relatively unstable, monosodium salt at ambient conditions, i.e. 20° C. and 1 atmosphere, and remains unstable at temperatures above about −20° C., wherein it undergoes dimerization and hydrolysis to form undesirable dimers and open ring by-products. Ahnarsson suggests a method of carbonation to converting the compound of formula I to a stable compound of formula II:

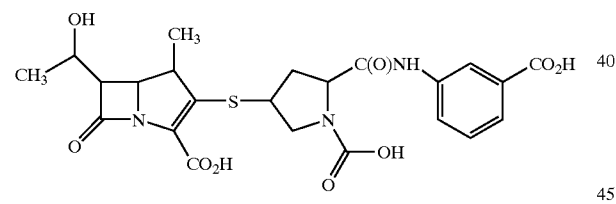

II

The method of stabilization requires the use of carbon dioxide, i.e. potassium, magnesium, calcium or sodium carbonates and bicarbonates as suitable carbon dioxide sources, and water or saline solution as a suitable solvent to produce the compound of formula II.

U.S. Pat. No. 5,952,323, to Zimmerman et al, issued Sep. 14, 1999, assigned to Merck & Co., Inc., teaches a more detailed process for converting the carbapenem monosodium salt into a stable carbapenem carbon dioxide adduct. In accordance with Zimmerman, specific mole ratios of sodium carbonate and sodium bicarbonate to unstabilized carbapenem monosodium salt, as well as pH limitations are suggested. The reference also provides solubility data for intravenous formulation at fixed conditions.

While Almarsson teaches reaction synthesis and conditions for preparation of the bulk carbapenem of formula I, and Zimmerman suggests $CO_2$ concentrations, pH and solubility ranges, neither reference provide a detailed step-by-step method for preparing a carbapenem formulation containing a stabilized $CO_2$ adduct of formula II. Due to the instability of the compound at temperatures above about −20° C., as well as its sensitivity to pH fluctuation, processing conditions for converting the bulk drug of formula I to the formulation of formula II are critical to providing a sterile, finish product of high quality.

It is now desirable to provide a process for converting a bulk drug, unstabilized carbapenem antibiotic, requiring storage at low temperatures, to a stabilized, carbapenem antibiotic, formulation suitable for intravenous and intramuscular injection into a patient in need thereof. It is also desirable to provide a product with needed solid state stability at room temperature and reconstitution stability for dosing.

SUMMARY OF THE INVENTION

The present invention is directed to a novel process for converting an unstabilized beta-lactam compound, i.e. carbapenem compound, more particularly a monosodium salt of a carbapenem compound, into a stabilized, beta-lactam compound, more particularly a stabilized, carbon dioxide adduct of carbapenem, and formulations thereof suitable for the treatment of bacterial infections in mammal patients, comprising the steps of:

a. preparing from about 1 to about 3N solution of sodium hydroxide, chilling the solution to a temperature of from about 0° to about 10° C.;

b. charging from about 40 to about 60% by wt., based on 100% by wt. total batch weight, of Water for Injection into a compounder having means for mixing, and cooling the water to a temperature of from about 0° to about 10° C.;

c. charging 1 mole equivalent of carbonates/active beta-lactam, wherein the carbonate are selected from sodium bicarbonate, sodium carbonate and mixtures thereof, into the compounder while mixing, to prepare a carbonate solution, while maintaining a temperature of from about 0° to about 10° C.;

d. maintaining the carbonate solution at a temperature range of from about 0° to about 10° C., and a pH of from 7.5 to about 9.0;

e. thawing a sufficient amount of unstabihized, beta-lactam from a temperature of about 20° C. to a temperature of from about 50 to about 25° C. to prepare a final, formulation containing about 200 g/liter of active beta-lactam, and charging at the same time into the compounder from about 0.7 to about 1.0 mole of sodium hydroxide/mole of active beta-lactam, while mixing the carbonate solution to dissolve the beta-lactam therein, and maintaining the compounder temperature of from about 0° to about 5° C. to produce a beta-lactam-carbonate solution;

f. adding the sodium hydroxide solution to the beta-lactam-carbonate solution, as required, during step e. to maintain the pH of the solution of from about 7.0 to about 8.0.

g. adding water, as required, to adjusting the beta-lactam-carbonate solution to a range of about 95 to about 97 weight %, based on 100 total weight %, and maintaining a temperature of from about 0° to about 5° C.;

h. adding the sodium hydroxide solution to the beta-lactam-carbonate solution, as required, to maintain the solution in a pH of from about 7.2 to about 7.8;

i. adding water, as required, to adjust the beta-lactam-carbonate solution to 100 weight % total, and maintaining the temperature of from about 0° to about 5° C.;

j. sealing the compounder containing the beta-lactam-carbonate solution and pressurizing to from about 10 to about 40 psig to initialize filtration;

k. filtering the beta-lactam-carbonate solution through a sterilizing filter into a continuously cooled, sterile, receiving vessel exhibiting a temperature of from about 0° to about 5° C. to produce a sterile, stabilized beta-lactam formulation;

l. aseptically filling the formulation into sterilized glass vials;

m. partially sealing the glass vials with dry, sterilized stoppers;

n. lyophilizing the solution by freezing in the glass vials at a temperature of from about −45° to about −40° C. to produce a frozen formulation;

o. primary drying the frozen formulation at a temperature of from about −25 to about −105° C. for about 48 to 60 hours at a pressure of 80 mTorr or lower;

p. secondary drying the formulation at a temperature from about 40° to about 60° C. at pressure of about 80mTorr or lower from about 3 to about 10 hours;

q. cooling the vials to ambient temperature; and r. sealing the vials under partial vacuum, while maintaining a temperature of about 25° C.

DETAILED DESCRIPTION OF THE INVENTION

Figure 1:
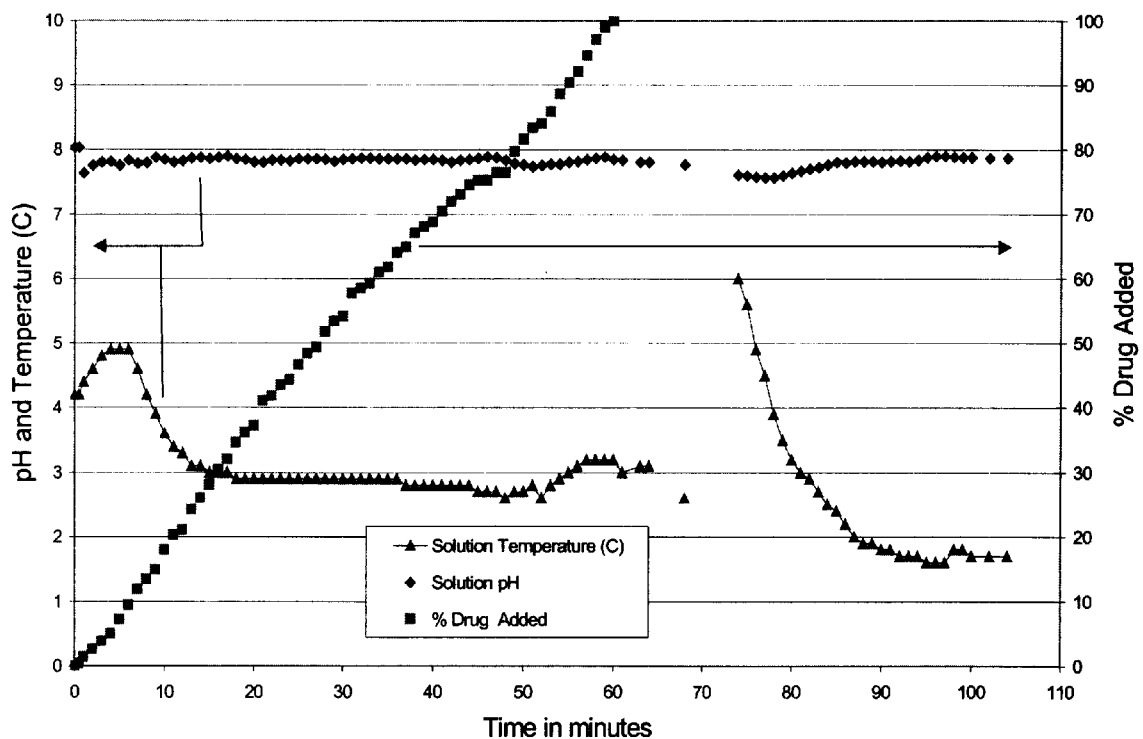
FIG. 1 is a graphical illustration of temperature and pH changes, and weight % of bulk drug addition during the compounding cycle of Example 1.

As used herein, the term "1 mole equivalent" is defined as 1 mole of carbonates per 1 mole of active drug, wherein carbonates a reselected from bicarbonates and carbonates, e.g. sodium bicarbonate, sodium carbonates, etc.

The term "bulk drug" "bulk active drug" or "bulk active beta-lactam" or "bulk active carbapenem," as use herein, is defined as the amount of actual unstable, beta-lactam, carbapenem and/or monosodium salt-containing carbapenem removed from cold storage.

The term "active drug," as used herein, is defined as the actual amount of beta-lactam, unstabilized and stabilized carbapenem, and monosodium salt-containing carbapenem and carbon dioxide-containing carbapenem. For example, the active drug is the amount of bulk drug less non-carbapenem, e.g. dimers and open ring by-products.

The term "quantum sufficit" ("q.s."), as used herein, is defined as the amount of a reagent necessary to increase the batch weight or volume to a specified total. As an example, a q.s. of 95% by wt. % means the amount of reagent required to bring the weight percent up to 95% by weight, based on 100% total weight.

The term "solid state stability", as used herein, is defined as the ability of finished, solid, lyophilized formulation (a porous off-white cake), at the end of about 2 years, to deliver the prescribed, labeled dosage of active drug.

The term "reconstitution stability", as used herein, is defined as the ability of a solution prepared by the finished, solid, lyophilized formulation into an appropriate diluent (i.e. 0.9% saline for injection, D5W, 1% Lidocaine, etc.) to deliver the prescribed, labeled dosage of active drug.

During the manufacture of bulk compound products such as beta-lactam and carbapenem antibiotics, the pharmaceutical compound is prepared by chemical synthesis from raw materials in large quantities. As with many carbapenem compounds, the compound in accordance with formula I is prepared in large batches as a monosodium salt. The compound is a weakly crystalline solid, hygroscopic at ambient conditions, and is unstable at room and refrigerated temperatures. Therefore, the bulk compound must be stored at a temperature of about −20° C. to prevent degradation into dimer and open ring by-products.

The unstable carbapenem, after bulk manufacturing can be stored for long periods of time at −20° C. and 1 atmosphere as a white powdery substance. However, this bulk compound must be converted into a stable formulation prior to use as once-a-day antimicrobial agent for intravenous (IV) and intramuscular (IM) administration.

The present invention is directed to a novel process for converting the unstable, monosodium salt of carbapenem antibiotic into stable, lyophilized carbon dioxide salt of carbapenem antibiotic that is suitable for the treatment of antibacterial infections in mammal patients. The references mention earlier herein address the bulk compound and method of preparing the carbon dioxide adduct, but fail to teach the conversion of the monosodium salt-containing compound to a formulation exhibiting acceptable levels of degradates required for solid state and reconstitution stability for dosing to patients.

The earlier mentioned references revealed that compound dimerization is inhibited via the formation of a reversible equilibrium adduct between carbon dioxide and monosodium salt of carbapenem compound of formula I, according to the following scheme:

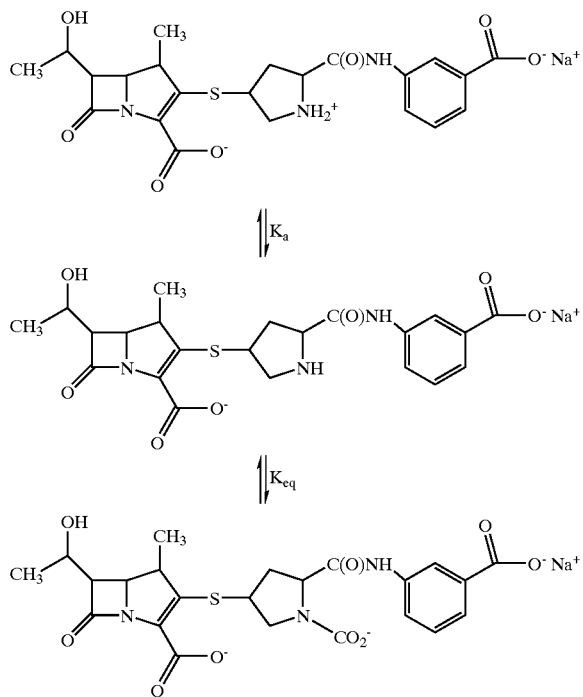

wherein $K_a$, and $K_{eq}$ are equilibrium constants of the reactions.

In accordance with the process of the present invention, unstable, carbapenem antibiotics are prepared into stabilized, carbapenem antibiotics suitable for the treatment of bacterial infections of patients in need thereof. More particular, the process converts unstable, monosodium salt of carbapenem antibiotic into stable, carbon dioxide adduct of carbapenem antibiotic formulation suitable for the treatment of bacterial infections in mammal patients. This sterile formulation can be administered intravenously or intramuscularly.

The batch-wise process of the invention, conducted under aseptic conditions, requires several reagents and processing units to prepare formulations of high quality, wherein the rate of conversion from the monosodium salt to the carbon dioxide adduct is high, and the formation of by-products, e.g. dimer and open ring compounds, is low. The mole ratio of sodium bicarbonate and sodium carbonate to active, bulk carbapenem, processing temperatures, pHs, mixing, and lyophilizing conditions are critical to the preparation of a formulation of high pharmaceutical quality.

The process for preparing a stable intravenous formulation of a carbon dioxide adduct of a carbapenem requires the processing temperature to be maintained within the range of about 0° to about 5° C. and the pH of the pre-lyophilized, active solution to be maintained within the range of about 7.0 to about 8.0. The process is conducted under aseptic conditions. All reagents utilized during the processes described herein meet United States Pharmacopeia and National Formulary standards unless otherwise noted.

The Reagents

Water for Injection United States Pharmacopeia (USP), $H_2O$, (hereinafter referred to as "WFI"), water purified by distillation or reverse osmosis having a molecular weight of 18.02 (CAS-7732-18-5), is utilized herein as a pharmaceutical solvent.

Sodium Hydroxide National Formulary (NF), NaOH, purified sodium hydroxide having a molecular weight of 40.00 (CAS-1310-73-2), is utilized herein as a pharmaceutical aid to control the pH of the reagents in the compounder/reactor. Generally, the pH is maintained in the alkaline region, e.g. pH of about 7.0 to about 9.0, throughout the cycling time of the process.

Sodium Bicarbonate United States Pharmacopeia (USP), $NaHCO_3$, purified carbonic acid monosodium salt having a molecular weight of 84.01 (CAS-144-55-8), is utilized herein as a primary source of alkalizing agent, i.e. carbonate.

Sodium Carbonate United States Pharmacopeia (USP), $Na_2CO_3$, purifed carbonic acid, disodium salt or disodium carbonate having a molecular weight of 105.99 (CAS-497-19-8), is utilized herein as a second source of alkalizing agent, i.e. carbonate.

The Process

Initially, a normal solution of from about 1 to about 3N sodium hydroxide is prepared by dissolving a sufficient amount of sodium hydroxide NF pellets in a sufficient amount of Water For Injection, USP. While adding the sodium hydroxide, the solution is constantly mixed to ensure complete dissolution. The compounder or reactor (up to 200L stainless steel jacketed vessel) utilized in the process is jacketed and cooled to maintain low temperatures and prevent bulk drug degradation during the process, and a variable agitation system is attached to the compounder to promote complete dissolution of the bulk drug into solution. Generally, about 40% by weight or 60% by volume of WFI is charged into the compounder to begin the process, and the water is cooled to the target temperature range of about 1° to about 5°C. To measure the pH of the solution in the compounder, appropriate pH and temperature devices are utilized; the pH meter is typically calibrated with buffers of pH 7.0 and 10.0. To control the pH during the batch-wise process, an appropriate pH Controller system equipped with a pump is utilized to meter NaOH solution into the compounder to maintain the pH within the required range.

After the WFI in the compounder is cooled, mixing is commenced to prevent localization of pH, temperature and concentration of reagents and bulk antibiotic drug. Sodium bicarbonate and/or sodium carbonate USP, in an amount sufficient to provide a final, formulation concentration thereof of about a 1 mole equivalent (defined above) is slowly added to the compounder under continuous mixing of the WFL. This solution is mixed until the carbonates are completely dissolved and the general pH of the solution is measured to ensure that it is between about 7.5 and about 9.0, preferably about 8.3, at a temperature in the range of about 0° to about 5° C., preferably about 2° C. The temperature and pH of the solution must be confirmed prior to beginning the addition of bulk drug. The unstable, bulk carbapenem drug is removed from a refrigerated unit held at about −20° C. and thawed to a temperature of from about 5° to about 25° C. for about 1 hour. A sufficient amount of the bulk drug is weighted out to provide a final formulation concentration of carbapenem of about 200 g of active drug (as free acid)/liter formulation. During the addition of the bulk active carbapenem to the compounder, the carbonate solution is constantly mixed. Generally, the mixing will begin at lower revolutions during the initial addition of bulk drug to the solution and as the amount of bulk in the solution is increased, the rpm of mixing is increased proportionally thereto. The primary purpose of mixing is to ensure complete dissolution of the bulk drug into the solution. As necessary, sodium hydroxide solution is added to the compounder during the addition of the bulk drug to maintain the solution within the target pH of about 7.0 to about 8.0, preferably a pH of about 7.5. The bulk drug is generally slowly added to the compounder at about a constant rate over a time period of from about 30 to about 90 minutes to enhance dissolution. At the end of the bulk drug addition, the solution is mixed for an additional time of about 5 minutes and complete dissolution thereof is confirmed. The q.s. of the batch weight is adjusted to about 95% by weight of the final weight of the formulation with WFI, if needed, wherein the temperature is maintained between about 0° and about 5° C. Further NaOH titration is performed over a 10 to 20 minute period to ensure a mole ratio of NaOH/bulk, active drug in the range of from about 0.7 to about 1.0, typically from about 0.75 to about 0.95, and preferably from about 0.8 to about 0.9. Finally, the batch is adjusted to 100% by weight of its final weight with WFI with moderate mixing.

Afterwards, the solution is filtered through a sterilizing filter of from about 0.2 to about 0.25 μm. When making larger batches, generally from about 10 to about 200 liters in a compounder, the compounding vessel is sealed and pressurized to initiate filtration. Filtration can be done either by pumping the solution through sterilizing filters with an appropriate pump in the absence of compounding vessel that can be pressurized or appropriate gas to carry out filtration by pressure. The receiving vessel for the filter formulation should be sterile and cooled to a temperature in the range of from about 0° to about 5° C. The filtered, formulation solution density will generally be from about 1.0 to about 1.2 g/ml at 0–5° C., typically about 1.1 g/ml. Next, the filtered formulation is filled into vials and partially sealed with dry, sterile siliconized lyophilization stoppers. In the following examples conventional 20 ml vials and 15 ml ADD-Vantage™ vials are utilized. The filled vials are placed onto lyophilizer shelves pre-cooled to a temperature of from about −40° to about −45° C., typically about −40° C.

The lyophilization cycles used herein for the different vials are described in the examples, below. Generally, the cycle requires the vials to be soaked at about −40° C. for about 2 hours and then heated to a temperature in the range of from about −25° to about −15° C. shelf temperature at a rate of about 0.5° C./minute. The temperature is normally held in a range of from about −25° to about −15° C., and the lyophilizer chamber pressure held at about 80 mTorr for a time period of from about 48 to about 60 hours. The vials are heated to about 10° C. shelf temperature at a rate of about 0.1° C./minute and then to about 40° C. shelf temperature at a rate of about 0.5° C./minute and held at 40° C. for up to about 3 hours at a pressure of about 80 mTorr or lower. Lastly, the vials are heated to about 60° C. shelf temperature at a rate of about 0.5° C./minute and held there at 80 mTorr or less for a time period of from about 3 to about 10 hours, and the shelves are cooled to ambient temperature (about 20° to about 30° C.). The vials are completely sealed under a partial vacuum of about 0.9 bar/700 Torr or lower before removing them from the lyophilizer. Finally, the vials are stored at a temperature not exceeding about 25° C. until needed.

In accordance with one preferred embodiment of the invention, there is described a novel process for preparing an intravenous formulation suitable for the treatment of bacterial infection, characterized as converting an unstabilized, carbapenem compound of formula I:

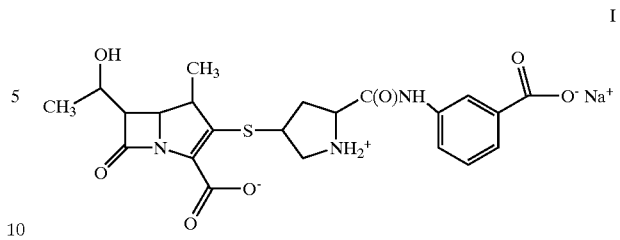

into a stabilized, carbapenem compound of formula II:

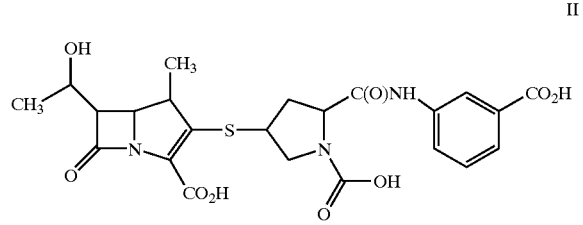

comprising the steps of:
a. preparing a solution of from about 1 to about 3N of sodium hydroxide and chilling the solution to a temperature of from about 0° to about 5° C.;
b. charging a total of from about 40 to about 60% by wt., based on 100% by wt. total of the batch weight of Water for Injection exhibiting a temperature of from about 2° to about 85° C. into a compounder having means for mixing, and cooling the water to a temperature of from about 0° to about 10° C.;
c. charging sufficient carbonate selected from sodium bicarbonate, sodium carbonate and mixtures thereof, into the compounder to prepare a final formulation exhibiting about 1 mole equivalent of carbonates/active carbapenem, dissolving the same, and maintaining the solution at a temperature range of from about 0° to about 5° C. to prepare a carbonate solution;
d. maintaining the carbonate solution at a pH of from about 7.5 to about 9.0, and a temperature of about 0° to about 50° C.;
e. thawing a sufficient amount of bulk carbapenem of formula I to provide a formulation exhibiting a concentration of about 200 g (as free acid)/l from a temperature of about −20° C. to about temperature of from about 5 to about 25° C., and slowly charging the same into the compounder with mixing of the carbonate solution to completely dissolve the bulk compound, while maintaining the compounder temperature of from about 0° to about 5° C. to produce an active carbapenem solution;
f. simultaneously adding the an about 1 to about 3N sodium hydroxide solution to the active carbapenem, as required during step e., and maintaining a pH of from about 7.0 to about 8.0;
g. adjusting the active carbapenem solution to about 95% by weight of the final product weight, based on 100 total weight percent, utilizing water for injection, as required and maintaining the bulk carbapenem solution in a temperature of from about 0° to about 5° C.;
h. adding the about 1 to about 3N sodium hydroxide solution to the bulk carbapenem solution to maintain a pH of from about 7.2 to about 7.8, as required;
i. adding Water for Injection, as required, to adjust the active carbapenem solution of 100% by wt., based 100% by wt. total weight, and maintaining a temperature of from about 0 to about 5° C.;

j. sealing and pressurizing the compounder containing the bulk compound solution to a pressure of about 15 to about 40 psig to initiate filtration;

k. filtering the bulk compound solution through a sterilizing filter into a continuously cooled, sterile, receiving vessel exhibiting a temperature of from about 0° to about 5° C.; and l. aseptically filling the intravenous formulation into sterile glass vials, and partially sealing the vials with dry, sterilized, lyophilization stoppers;

m. lyophilizing the formulation by freezing in the glass vials at a temperature of from about −45° to about −40° C. to produce a frozen formulation;

n. primary drying the frozen formulation at a temperature of from about −25° to about −15° C. for about 48 to 60 hours at a pressure of about 80 mTorr or lower;

o. secondary drying the formulation at a temperature of from about 40° to about 60° C. at a pressure of about 80 mTorr or lower for a time period of from about 3 to about 10 hours;

p. cooling the vials to ambient temperature; and q. sealing the vials under a partial vacuum of about 0.9 bar/700 Torr or lower, while maintaining a temperature of about 25° C., wherein the stabilized, carbapenem antibiotic formulation of formula II exhibits a carbapenem concentration of about 200 g/l and a carbonate content of about 1 mole equivalent.

The following examples are provided for illustrative purposes and should not be construed as limiting the invention disclosed herein.

EXAMPLE 1

At ambient temperature and pressure, a 2N sodium hydroxide solution was prepared by dissolving 20 g of sodium hydroxide NF pellets in 250 ml of water for injection (WFI) while mixing. A Beckman pH probe was calibrated using pH 7 and 10 buffers. Into a Kontes 317000–1000, one (1) liter glass, compounder/reactor vessel with jacketed cooler and agitator was charged 400 ml of WFI (about 50% of total batch volume), which was cooled to 5° C. Thereafter, 28.0 g of sodium bicarbonate USP were dissolved into the compounder, and the compounder was held at a temperature of between 1° and 5° C., and a pH of between 8.1 and 8.5.

Figure 2:
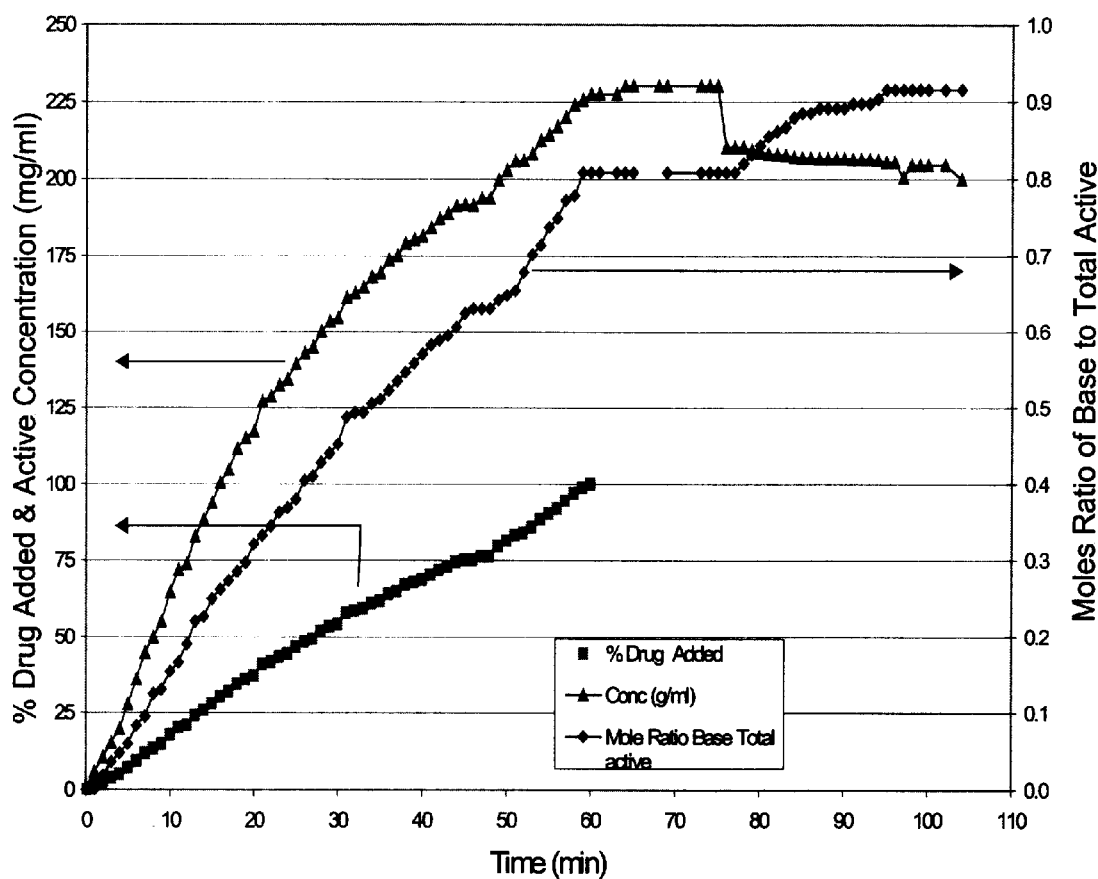
FIG. 2 is a graphical illustration of weight % of bulk monosodium salt-containing carbapenem added, active concentration, and mole ratio of sodium hydroxide (base) to mole of active carbapenem during the compounding cycle of Example 1.

Unstable carbapenem, bulk drug substance, 160 g of free acid exhibiting a moisture content of about 17.0% by weight, was thawed to room temperature from −20° C. for 30 minutes. To reduce localization of pH, the 2N solution of sodium hydroxide was metered sub-surface into the compounder by a Masterflex peristaltic pump through size 16 tubing and a one (1) foot long×1/16 inches diameter stainless steel dip tube. The bulk drug was divided into ten (10) equal portions and gradually added to the sodium bicarbonate solution over a 60 minutes period to ensure complete dissolution. FIG. 1 depicts the pH and temperature fluctuations during the bulk drug addition to the compounder. During the addition of the bulk drug, the sodium bicarbonate solution was constantly agitated. The solution temperature was maintained between 1° and 6° C. and the pH at a set point of 7.8 by the addition of sodium hydroxide solution (see FIG. 1). Following the addition of the bulk drug, the batch weight was adjusted to 95% of the final weight with WFI maintained at a temperature of 1° to 5° C. to produce a bulk drug-sodium bicarbonate solution. While the bulk drug-sodium bicarbonate solution was agitated for an additional 20 minutes, 2N sodium hydroxide titrations were performed to achieve a mole ratio of sodium hydroxide to bulk drug of 0.93. The final weight of the batch was adjusted to 100% total with chilled WFI at 1° to 5° C. with additional agitation for 5 minutes. The total drug addition and compounding time was 102 minutes, and final batch weight was 888.0 g. FIG. 2 provides the bulk drug concentration, % bulk drug added during compounding, and the mole ratio of base (H) to total active drug, wherein "total active drug" is the concentration of carbapenem within the batch.

While maintaining the solution at a temperature between 1° and 5° C., the bulk drug-sodium bicarbonate solution was filtered utilizing a Sterivex GV filter unit containing a 0.22 µm filter into a sterile plastic container using a peristaltic pump. Immediately thereafter, 6.33 g of the solution was placed into conventional 20 ml vials utilizing a manual filler, and the vials were frozen to −70° C. The vials were partially stoppered and placed onto the shelves of a Virtis Lyophilizer pre-cooled to −40° C. Thereafter, the lyophilizer was operated according to the following cycle:

i) soak at −40° C. shelf temperature for 2 hrs;

ii) heat to −20° C. shelf temperature at rate of 0.5° C./min;

iii) hold shelf temperature at −20° C. and 80 mTorr pressure for 48 hrs;

iii) heat to 10° C. shelf temperature at rate of 0.1° C./min;

iv) heat to 40° C. shelf temperature at rate of 0.5° C./min;

v) hold at 40° C. and 80 mTorr for 3 hrs;

vi) heat to 60° C. shelf temperature at rate of 0.5° C./min;

vii) hold at 60° C. and 80 mTorr for 3 hrs;

viii) cool the shelves to ambient temperature (20°–30° C.); and ix) stopper under partial vacuum of 0.9 bar/700 Torr.

Figure 3:
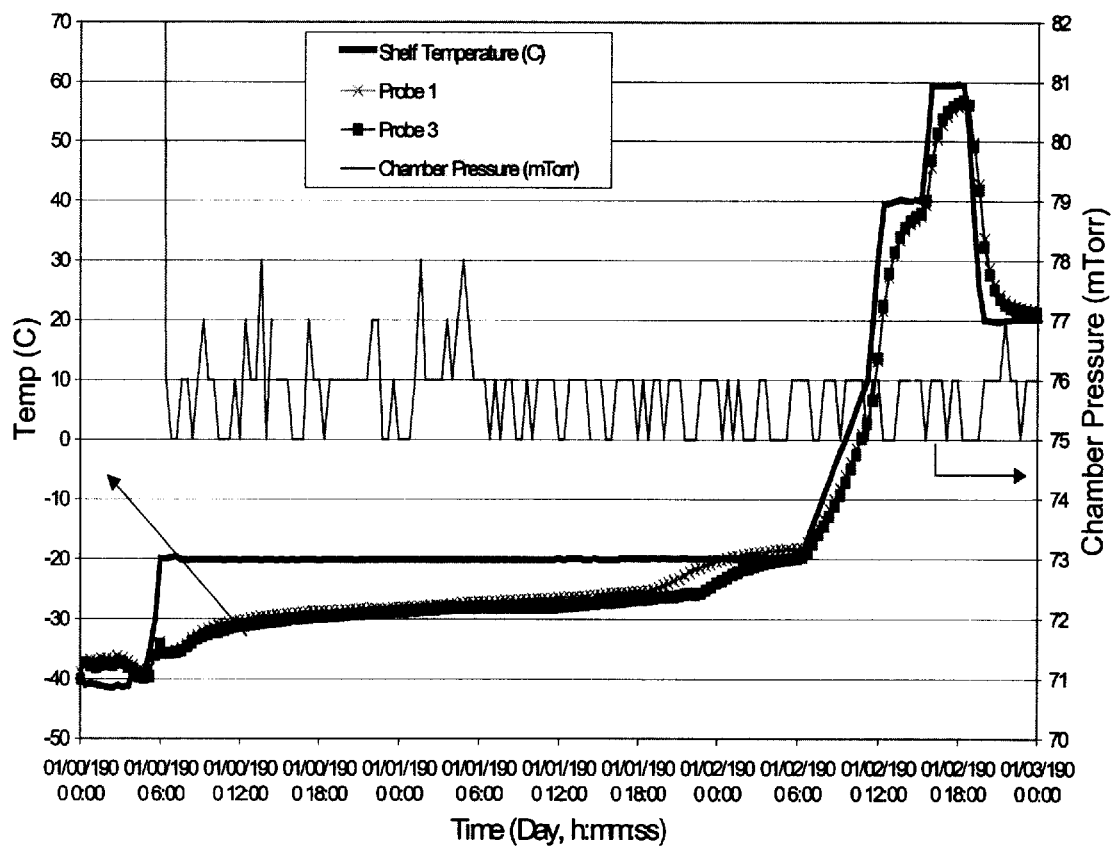
FIG. 3 is a graphical illustration of the pressure and temperature changes during the lyophilization cycles of Examples 1 and 2.

FIG. 3 illustrates the shelf temperature and chamber pressure values during the lyophilization cycle for Examples 1 and 2.

Finally, the vials were removed from the lyophilizer as the final formulation. Upon analysis, the formulation exhibited the following characteristics listed in Table 1:

TABLE 1

| Component | g/liter | g/0.8 liter |
|---|---|---|
| Carbapenem | 200.0* | 160.0* |
| Sodium Bicarbonate USP | 35.0 | 28.0 |
| Sodium Hydroxide NF** | adjusted to pH 7.8 | adjusted to pH 7.8 |
| Water for Injection USP*** | q.s 1.00 liter | q.s. 0.8 liter |

*as free acid;
**diluted in Water for Injection USP, and used as 2N solution for pH control;
***removed during lyophilization The final product exhibited a moisture content of 1.91% w/w. Table 2 illustrates the High Performance Liquid Chromatography (HPLC) results in area % of in process samples collected during the production of stabilized carbapenem antibiotic for this example.

TABLE 2

| | Carbapenem | Total Degradates | Total Dimers | Ring Open |
|---|---|---|---|---|
| | | HPLC, Area % | | |
| Bulk drug | 98.6 | 1.4 | 0.5 | 0.7 |
| Prefilter Soln. | 97.6 | 2.3 | 1.1 | 1.0 |

TABLE 2-continued

|  | Carbapenem | Total Degrades HPLC, Area % | Total Dimers | Ring Open |
|---|---|---|---|---|
| End of Vial Filling | 96.8 | 3.0 | 1.5 | 1.4 |
| Lyophilized Product | 95.6 | 4.4 | 1.6 | 2.5 |

EXAMPLE 2

Figure 4:
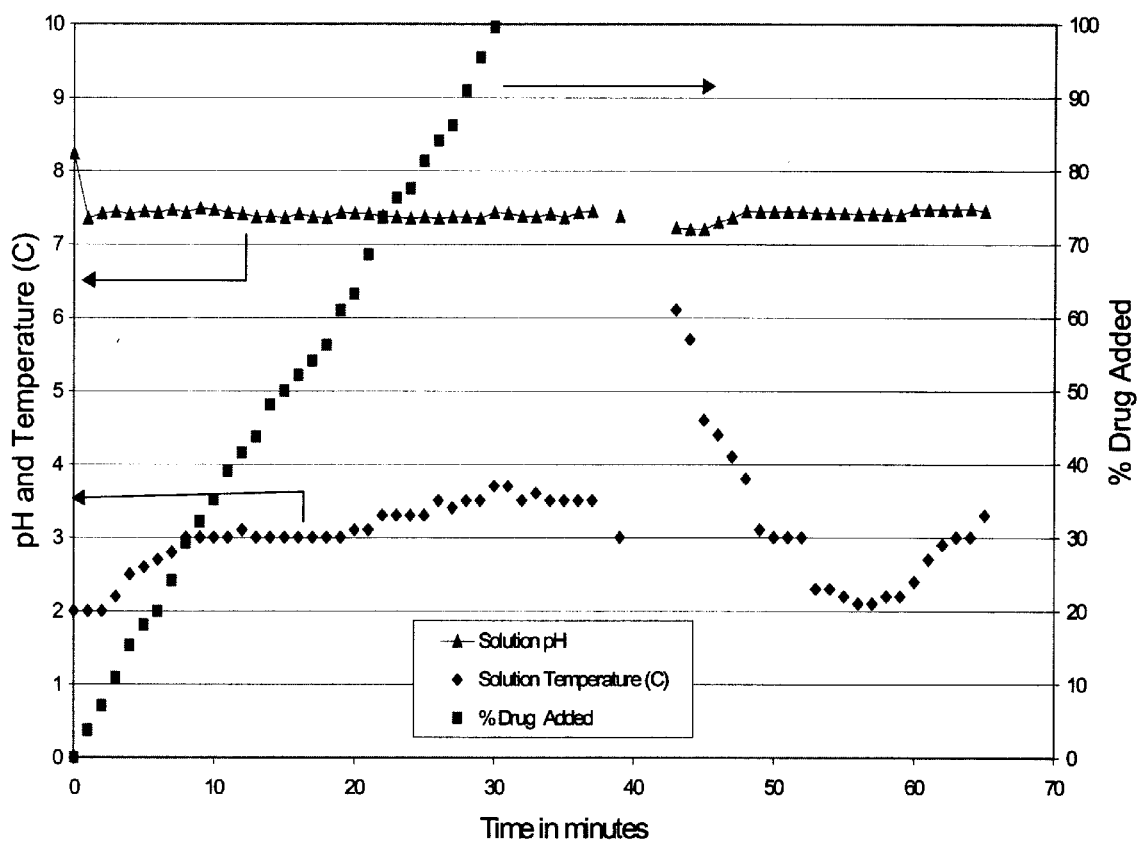
FIG. 4 is a graphical illustration of the temperature and pH change, and weight % of bulk drug addition during the compounding cycle of Example 2.
Figure 5:
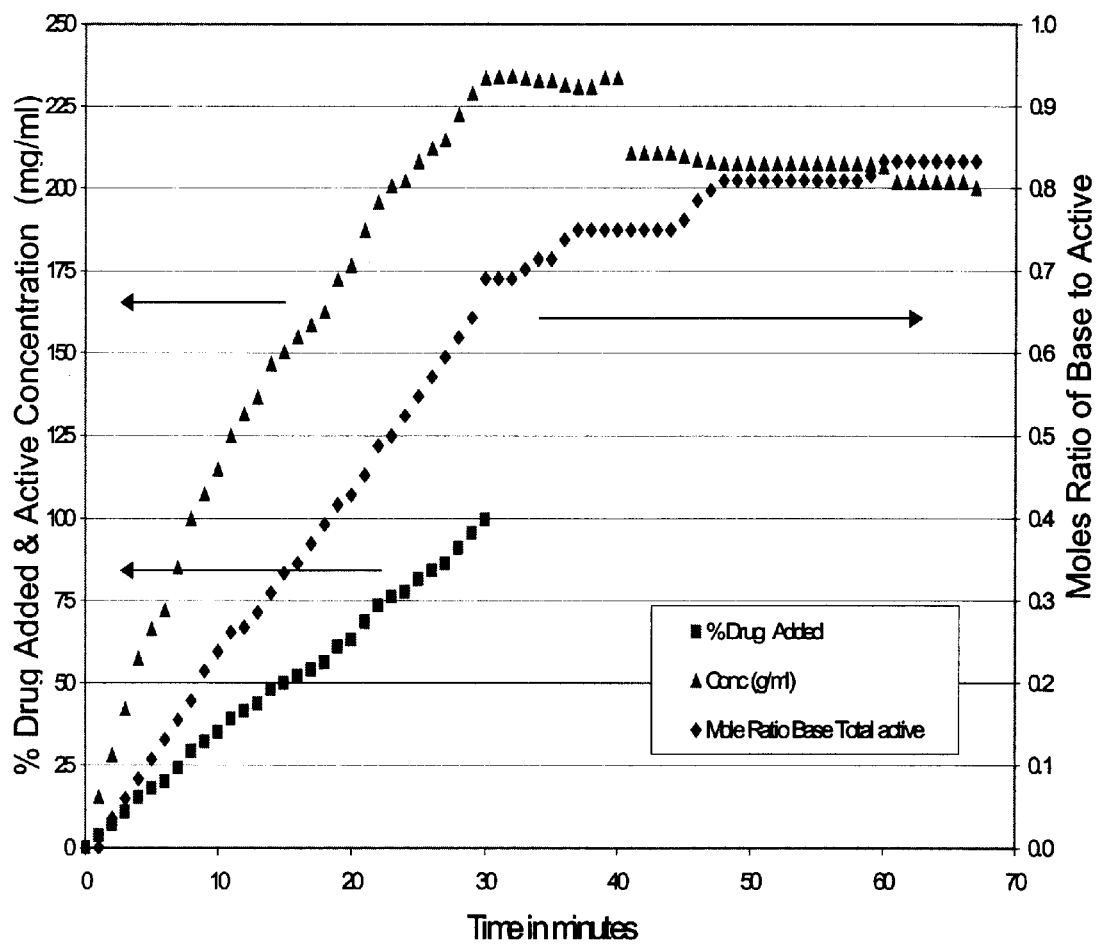
FIG. 5 is a graphical illustration of weight % of bulk monosodium salt-containing carbapenem added, active concentration, and mole ratio of sodium hydroxide (base) during the compounding cycle of Example 2.
Figure 6:
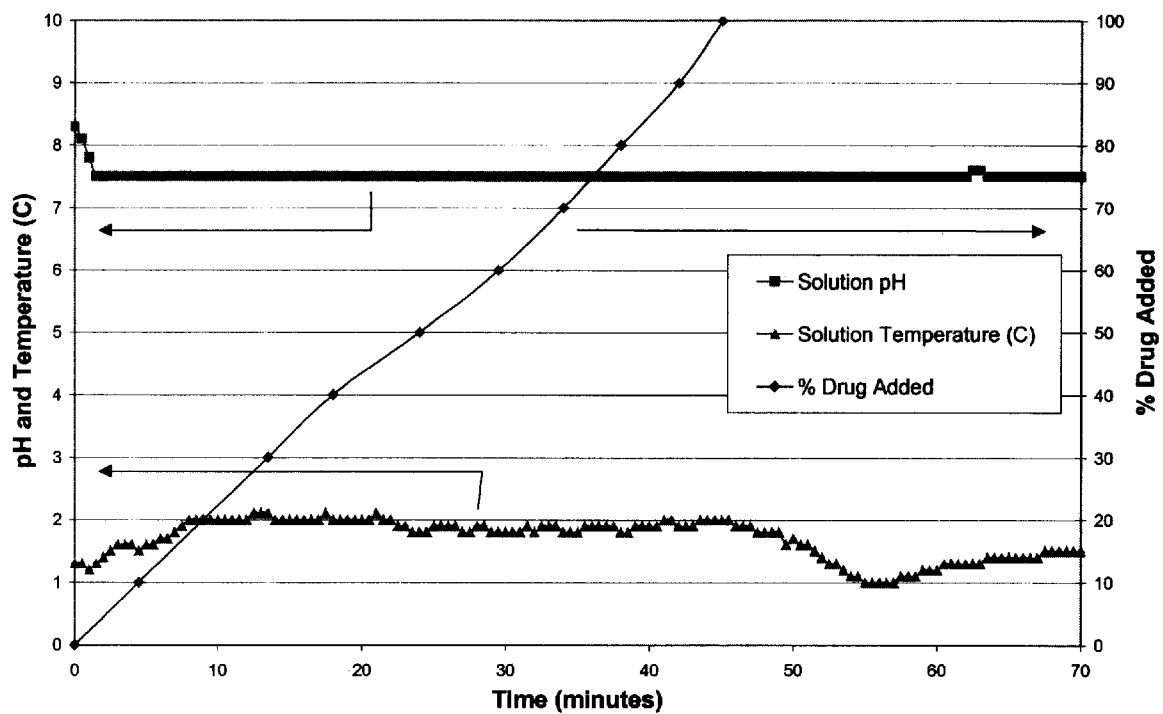
FIG. 6 is a graphical presentation of temperature and pH changes, and weight % of bulk drug addition during the compounding cycle of Example 3.
Figure 7:
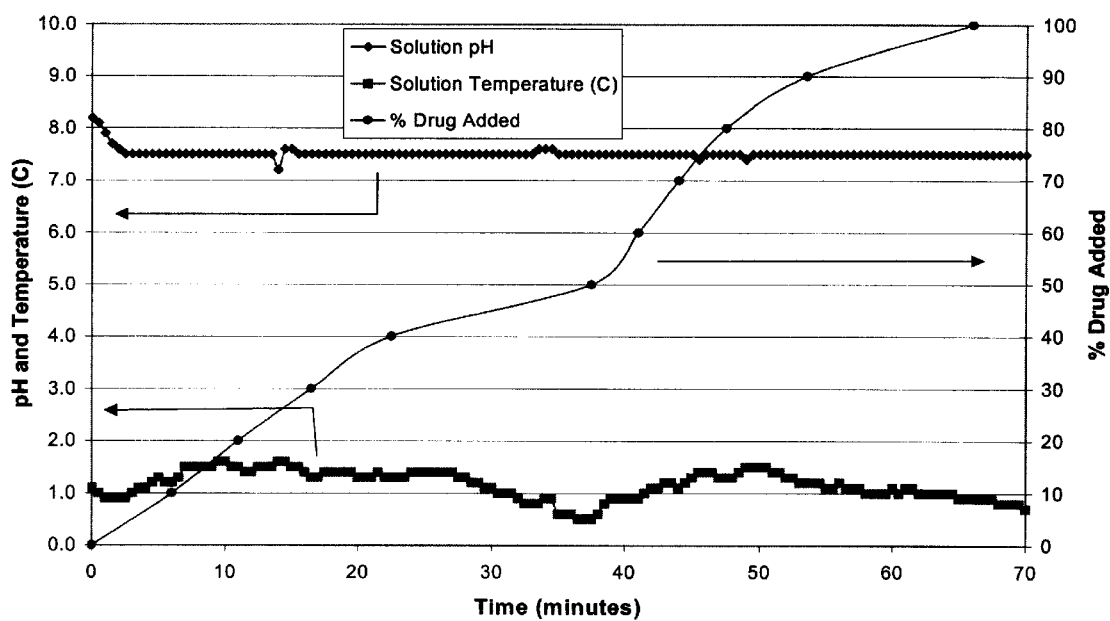
FIG. 7 is a graphical illustration of temperature and pH changes, and weight % of bulk drug addition during the compounding cycle of Example 4.
Figure 8:
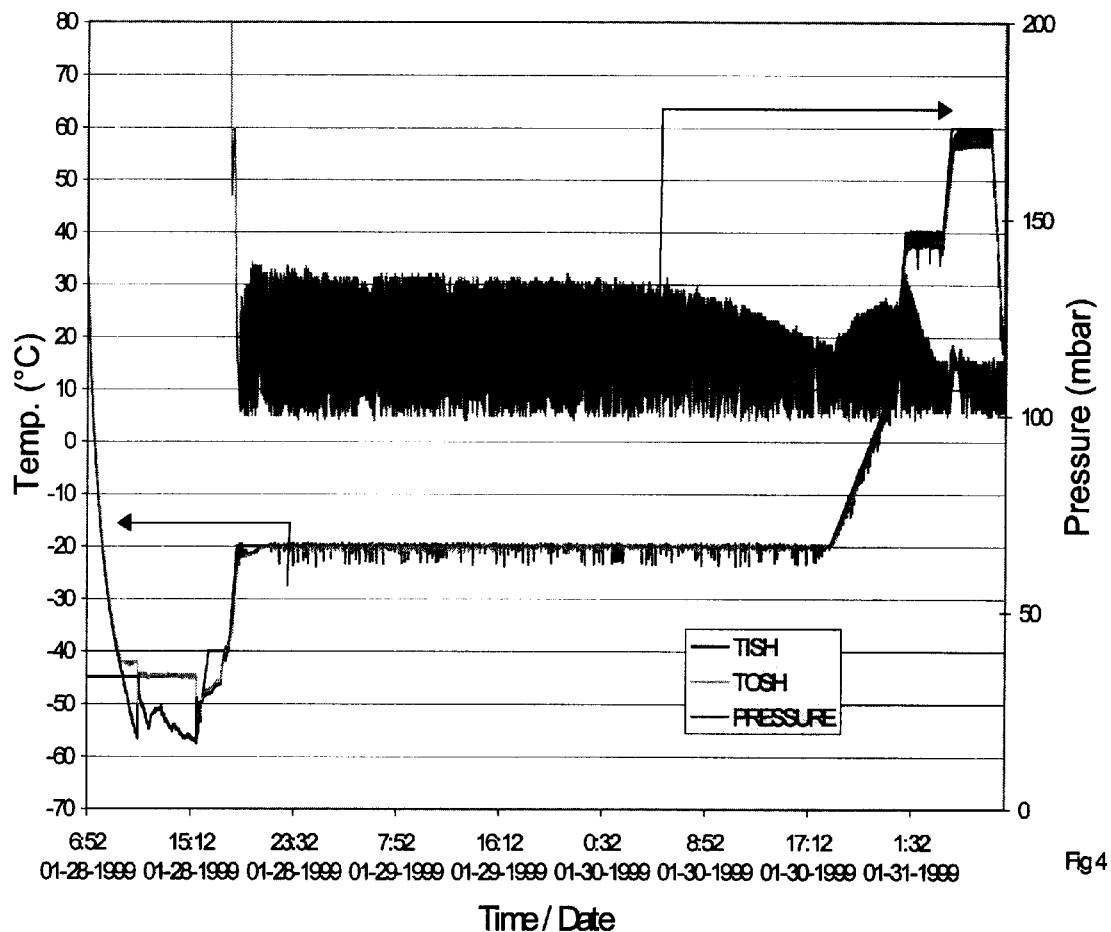
FIG. 8 is a graphical illustration of the pressure and temperature changes during the lyophilization cycles of Example 3.
Figure 9:
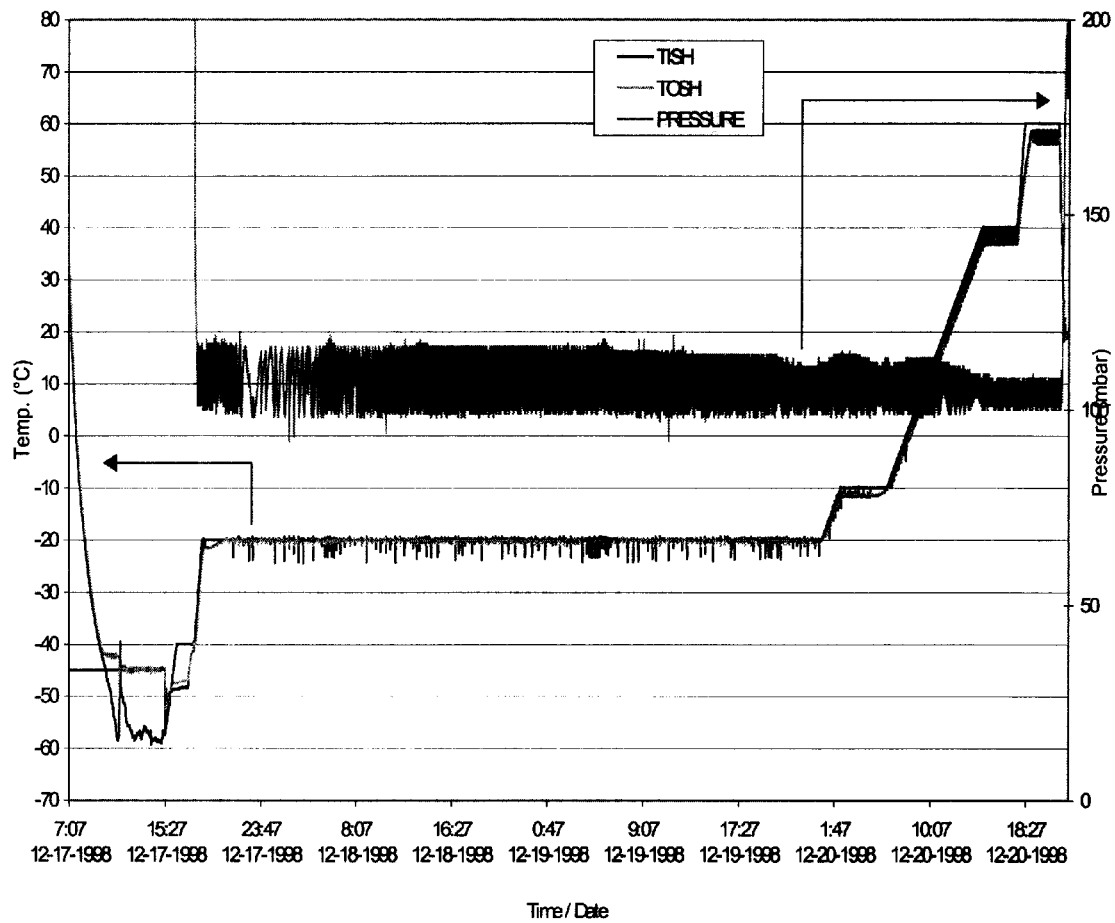
FIG. 9 is a graphical illustration of the pressure and temperature changes during the lyophilization cycle of Example 4.

The general procedure described in Example 1 was utilized to prepare the formulation of this example. FIG. 4 illustrates the pH and temperature fluctuations during the total compounding time, and % weight of bulk drug, bulk drug added to the compounder during the compounding period. Except for the values provided in Table 3, identical conditions were utilized in both examples. FIG. 5 provides data for the mole ratio of base to active bulk drug, as well as % bulk drug added to the compounder and active drug concentration during the compounding time. The final product exhibited a moisture content of 1.87% w/w. Table 4 illustrates the HPLC results in area % of in process samples collected during the production of stabilized carbapenem antibiotic for this example.

TABLE 3

| Drug Addition Time, minutes | 30 |
|---|---|
| Total Compounding Time, minutes | 68 |
| pH SetPoint during Compounding | 7.4 |
| Mole Ratio of NaOH/Drug | 0.83 |

TABLE 4

|  | Carbapenem | Total Degrades HPLC, Area % | Total Dimers | Ring Open |
|---|---|---|---|---|
| Carbapenem | 98.5 | 1.5 | 0.7 | 0.7 |
| Prefilter Soln. | 98 | 1.9 | 0.9 | 0.9 |
| End of Fill | 97.3 | 2.5 | 1.2 | 1.2 |
| Lyophil' Prod. | 95.9 | 4.1 | 1.5 | 2.3 |

EXAMPLES 3 AND 4

Examples 3 and 4 were conducted utilizing the same basic procedures described herein below, with the exception of the parameters given in Table 5, below. However, the vial utilized in Example 3 were conventional, while those utilized in Example 4 were ADD-Vantage™ vials.

To prepare a pilot plant batch of the formulation, a 2N solution of sodium hydroxide was prepared by dissolving 250 g of sodium hydroxide NF pellets in 2,000 g of WFI while mixing, the solution was cooled to ambient temperature, and WFI was added to produce the final solution of 3,406 g. The sodium hydroxide solution was chilled utilizing an Isotemp 1028S Chiller to a temperature of 4° C. Into a 20 liter, stainless steel, jacketed compounder, 6.42 kg of the WFI was charged, and the solution was cooled to a target temperature of 1° to 5° C. The pH probe attached to a HD-PH-P pH Controller was standardized using pH 7.0 and 10.0 buffer solutions.

Sodium bicarbonate USP in an amount of 448 g was dissolved in the compounder while continuously stirring until complete dissolution occurred, wherein the pH of the solution measured 8.3. Thereafter, the unstabilized bulk drug (as anhydrous free acid) in an amount of 2560 g was thawed from −20° C. to ambient temperature for approximately 1 hour and then divided into 10 equal portions. The 10 portions of bulk drug were added to the compounder over a 60 minute period, while adding the sodium hydroxide solution via the pH controller to keep bulk drug solution in the compounder close to the a target pH of 7.6. At the end of the bulk drug addition, the solution was mixed for an additional 15 minutes, and 2N NaOH titrations were preformed to confirm complete dissolution of the bulk drug. After mixing for an another 15 minutes, water for injection at a temperature of 0° to 8° C. was added to bring the solution to about 97% of the total weight, based on 100 total weight percent. While still mixing the solution, the pH thereof was adjusted to 7.7 by addition of 2N NaOH solution, ensuring that the mole ration of NaOH to bulk drug is within the range of 0.8 to 0.9. The weight of the solution was adjusted to 100 weight percent of the final batch weight by addition of WFI at a temperature of from 0° to 8° C. while mixing for another 5 minutes. The compounder was then sealed and pressurized to 15 psig to initiate filtration, and the solution was filtered through a Millipak 0.22 μm sterilizing filter into a sterile receiving vessel, continuously cooled to a temperature for from 1° to 5° C. The filtered, formulation solution exhibited a density of about 1.11 g/ml at 5° C.

The sterile formulation was placed into sterile glass vials (6.33 g into 20 ml conventional vials, and 5.77 g into 15 ml ADD-Vantage). The filled vials were partially stoppered with dry, sterile, siliconized lyophilization stoppers, and placed onto lyophilizer shelves pre-cooled to a temperature of from −45° to −40° C. The lyophilizing procedure was conducted as follows:

20 ml Conventional Vials
 a. soak at −40° C. (range −45° to −40° C.) lyo shelf temperature for at least 2 hours;
 b. heat to −20° C. shelf temperature at 0.5° C./minute;
 c. hold shelf temperature at −20° C. and 80 mTorr pressure for 48 hours;
 d. heat to 10° C. shelf temperature at 0.1° C./minute;
 e. heat to 40° C. shelf temperature at 0.5° C./minute; hold at 40° C. and 80 mTorr for 3 hours;
 f. heat to 60° C. shelf temperature at 0.5° C./minute; hold at 60° C. and 80 mTorr for 3 hours;
 g. cool the shelves to ambient temperature (20°–30° C.) before unloading; and h. stopper under partial vacuum (target of 0.9 bar/700 Torr).

ADD-Vantage Vials
 a. soak at −40° C. (range −45° to −40° C.) lyophilizer shelf temperature for at least 2 hours;
 b. heat to −20° C. shelf temperature at 0.5° C./minute;
 c. hold shelf temperature at −20° C. and 80 mTorr pressure for 54 hours;
 d. heat to −10° C. shelf temperature at 0.1° C./minute; hold at −10C and 80 mTorr for 4 hours;
 e. heat to 10° C. shelf temperature at 0.1° C./minute;
 f. heat to 40° C. shelf temperature at 0.5° C./minute; hold at 40° C. and 80 mTorr for 3 hours;
 g. heat to 60° C. shelf temperature at 0.5° C./minute; hold at 60° C. and 80 mTorr for 3 hours;
 h. cool the shelves to ambient temperature (20–30° C.) before unloading; and
 i. stopper under partial vacuum (target of 0.9 bar/700 Torr).

After completion of the lyophilizing step, the vials containing the formulation were removed from the lyophilizer and capped (flip-off caps for conventional vials and ADD-Vantage caps for ADD-Vantage vials). Finally, the vials were stored at a temperature of 25° C. or cooler.

TABLE 5

| Image | Example 3 | Example 4 |
|---|---|---|
| Drug Addition Time, min | 45 | 66 |
| Total Compounding Time, min | 114 | 134 |
| pH Controller Setpoint During Drug Addition | 7.6 | 7.6 |
| pH Controller Setpoint During pH Adjustment | 7.7 | 7.7 |
| Mole Ratio of NaOH Added to Active Drug | 0.85** | 0.87** |
| Filtration Time, min | 30 | 31 |
| Vial Filling Time, min | 203 | 157 |
| Lyophilizer Cycle Time, min | 65 | 78 |

The final stabilized carbapenem antibiotic formulation was analyzed to contain the amount of components listed in Table 6, below

TABLE 6

| Component | g/liter | g/0.8 liter |
|---|---|---|
| Carbapenem | 200.0* | 160.0* |
| Sodium Bicarbonate USP | 35.0 | 28.0 |
| Sodium Hydroxide NF** | adjusted to pH 7.8 | adjusted to pH 7.8 |
| WFI USP*** | q.s. 1.00 liter | q.s. 0.8 liter |

Table 7 summarizes the BPLC results of area percent of in-processing samples collected during production of the batch of Example 3.

TABLE 7

| | Carbapenem | Total Degradates | Total Dimers | Ring Opening |
|---|---|---|---|---|
| | | HPLC, Area % | | |
| Bulk Carbapenem | 99.2 | 0.7 | 0.4 | 0.3 |
| Pre-filtered Solution | 97.6 | 2.2 | 1.0 | 1.2 |
| Beginning of Vial Filling | 96.9 | 3.0 | 1.6 | 1.4 |
| Middle of Vial Filling | 96.3 | 3.0 | 1.6 | 1.4 |
| End of Vial Filling | 95.7 | 4.3 | 2.5 | 1.7 |
| Beginning of Lyophilization | 95.5 | 4.4 | 1.7 | 2.5 |
| Middle of Lyophilization | 95.2 | 4.6 | 1.9 | 2.5 |
| End of Lyophilization | 94.7 | 5.2 | 2.3 | 2.7 |

The weight percent of moisture per 100% total weight, as determined by NIR for Examples 3 and 4 were 1.8 and 2.1, respectively.

The principles of the process and formulations, preferred embodiment and modes of operation of the present invention have been described in the foregoing specification. However, the invention disclosed as intended to be protected is not to be construed as limited to the particular embodiments disclosed. The embodiments are to be construed as illustrative rather than restrictive. It is recognized, however, that departures may be made therefrom within the scope of the invention, and that obvious modifications may occur to a person skilled in the art.

What is claimed is:

1. A process for stabililzing a beta-lactam carbapenem formulation for the treatment of bacterial infections in mammal patients, comprising the steps of:

a. preparing a solution of about 1 to about 3N sodium hydroxide, chilling the solution to a temperature of from about 0° to about 10° C.;

b. charging from about 40 to about 60% by wt., based on 100% by wt. total batch weight, of Water for Injection into a compounder having means for mixing, and cooling the water to a temperature of from about 0° to about 10° C.;

c. charging 1 mole equivalent of carbonate/active beta-lactam carbapenem, wherein the carbonate are selected from sodium bicarbonate, sodium carbonate and mixtures thereof, into the compounder while mixing, to prepare a carbonate solution, while maintaining a temperature of from about 0° to about 10° C.;

d. maintaining the carbonate solution at a temperature range of from about 0° to about 10° C., and a pH of from 7.5 to about 9.0;

e. thawing a sufficient amount of a first beta-lactam carbapenem from a temperature of about −20° C. to a temperature of from about 5° to about 25° C. to prepare a final, formulation containing about 200 g/liter of active beta-lactam carbapenem, and charging at the same time into the compounder from about 0.7 to about 1.0 mole of sodium hydroxide/mole of active beta-lactam carbapenem, while mixing the carbonate solution to dissolve the beta-lactam carbapenem therein, and maintaining the compounder temperature of from about 0° to about 5° C. to produce a second beta-lactam carbapenem carbonate solution;

f. adding the sodium hydroxide solution to the second beta-lactam carbapenem carbonate solution, as required, during step e. to maintain the pH of the solution of from about 7.0 to about 8.0;

g. adding water, as required, to adjusting the second beta-lactam carbapenem carbonate solution to a range of about 95 to about 97 weight %, based on 100 total weight %, and maintaining a temperature of from about 0° to about 5° C.;

h. adding the sodium hydroxide solution to the second beta-lactam carbapenem carbonate solution, as required, to maintain the solution in a pH of from about 7.2 to about 7.8;

i. adding water, as required, to adjust the second beta-lactam carbapenem carbonate solution to 100 weight % total, and maintaining the temperature of from about 0° to about 5° C.;

j. sealing the compounder containing the second beta-lactam carbapenem carbonate solution and pressurizing to from about 10 to about 30 psig to initialize filtration;

k. filtering the second beta-lactam carbapenem carbonate solution through a sterilizing filter into a continuously cooled, sterile, receiving vessel exhibiting a temperature of from about 0° to about 5° C. to produce a final sterile, beta-lactam carbapenem formulation;

l. aseptically filling the formulation into sterilized glass vials;

m. partially sealing the glass vials with dry, sterilized stoppers;

n. lyophilizing the solution by freezing in the glass vials at a temperature of from about −45° to about −40° C. to produce a frozen formulation;

o. primary drying the frozen formulation at a temperature of from about −25 to about −15° C. for about 48 to 60 hours at a pressure of about 80 mTorr or lower;
p. secondary drying the formulation at a temperature from about 40° to about 60° C. at pressure of about 80 mTorr or lower for from about 3 to about 10 hours;
q. cooling the vials to ambient temperature; and
r. sealing the vials under a partial vacuum, while maintaining a temperature of about 25° C.

2. The process according to claim 1, wherein the first beta-lactam carbapenem compound is a monosodium salt of a carbapenem.

3. The process according to claim 2, wherein the final sterile beta-lactam carbapenem compound is carbon dioxide adduct of a carbapenem.

4. The process according to claim 2, wherein the monosodium salt of a carbapenem is of formula I:

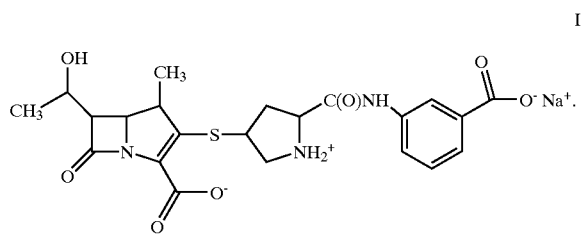

5. The process according to claim 3, wherein the carbon dioxide adduct of a carbapenem is of formula II:

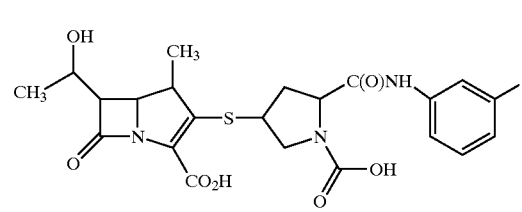

6. The process according to claim 1, wherein the concentration of sodium bicarbonate to water in the solution is about 35 g/liter.

7. The process according to claim 1, wherein the pH of sodium bicarbonate solution is about 8.25.

8. The process according to claim 4, wherein the compound of formula I exhibits a moisture content of up to about 20.0% by weight.

9. The process according to claim 6, wherein the sodium hydroxide solution is high velocity injected into the compounder.

10. The process according to claim 7, wherein the reaction vessel is pressurized to a pressure of about 15 psig.

11. The process according to claim 8 wherein, the sterilizing microfilter is about 0.22 μm.

12. The process according to claim 9, wherein the lyophilizing step, comprises:
a. cooling the vials to a temperature of from about −45° to about −40° C. for about 2 hours;
b. heating the vials to a temperature of about −20° C. at a rate of about 0.5° C./minute, and maintaining the vial temperature at about −20° C., while maintaining a pressure of from about 65 to about 95 mTorr for about 48 hours;
c. heating the vials to a temperature of about 10° C. at a rate of about 0.1° C./min;

d. heating the vials to a temperature of about 40° C. at a rate of about 0.5° C./min, and hold at about 40° C., while maintaining a pressure of about 80 mTorr or lower for up to about 3 hours;
e. heating the vials to a temperature of about 60° C. at a rate of about 0.5° C./min, and hold at about 60° C. and about 80 mTorr or lower for about 5 hours; and
f. cooling the vials to a temperature of from about 20° to about 30° C.

13. The process according to claim 10, wherein the vials are sealed under a partial vacuum of about 700 Torr or lower.

14. The process according to claim 11, wherein the final sterilized carbapenem of formula II exhibits a carbapenem concentration of 200 g/liter, and a sodium bicarbonate concentration of 35.0 g/liter.

15. A process for converting a carbapenem compound of formula I:

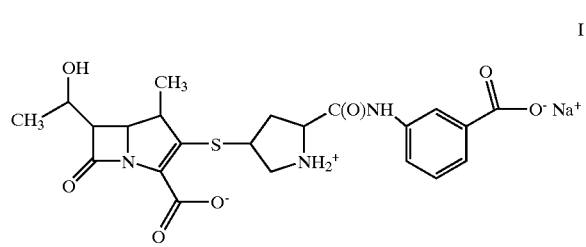

into a carbapenem compound of formula II:

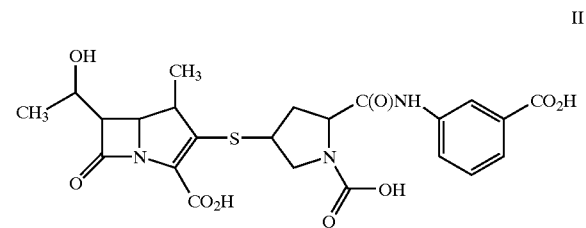

comprising the steps of:
a. preparing a solution of from about 1 to about 3N of sodium hydroxide and chilling the solution to a temperature of from about 0° to about 10° C.;
b. charging a total of from about 40 to about 60% by wt., based on 100% by wt. total of the batch weight of Water for Injection exhibiting a temperature of from about 20 to about 85° C. into a compounder having means for mixing, and cooling the water to a temperature of from about 0° C. to about 5° C.;
c. charging sufficient carbonate selected from sodium bicarbonate, sodium carbonate and mixtures thereof, into the compounder to prepare a final formulation exhibiting 1 mole equivalent of carbonate/active carbapenem, dissolving the same, and maintaining the solution at a temperature range of from about 0° to about 5° C. to prepare a carbonate solution;
d. maintaining the carbonate solution at a pH of from about 7.5 to about 9.0, and a temperature of about 0° to about 5° C.;
e. thawing a sufficient amount of bulk carbapenem of formula I to provide a formulation exhibiting a concentration of about 200 g/l from a temperature of about −20° C. to about temperature of from about 5 to about 25° C., and slowly charging the same into the compounder with mixing of the carbonate solution to completely dissolve the bulk compound, while maintaining the compounder temperature of from about 0° to about 5° C. to produce an active carbapenem solution;

f. adding the sodium hydroxide solution to the active carbapenem, as required during step e., and maintaining a pH of from about 7.0 to about 8.0;

g. adjusting the active carbapenem solution to 95% by weight of the final product weight, based on 100 total weight percent, utilizing water for injection, as required and maintaining the bulk carbapenem of formula I solution in a temperature of from about 0° to about 5° C.;

h. adding the sodium hydroxide solution to the bulk carbapenem of formula I solution to maintain a pH of from about 7.2 to about 7.8;

i. adding Water for Injection, as required, to adjust the active carbapenem solution to q.s. of 100% by wt., based 100% by wt. total weight, and maintaining a temperature of from about 0 to about 5° C.;

j. sealing and pressurizing the compounder containing the bulk compound of formula I solution to about 15 psig to initiate filtration;

k. filtering the bulk compound of formula I solution through a sterilizing filter into a continuously cooled, sterile, receiving vessel exhibiting a temperature of from about 0° to about 5° C. producing a final sterile beta-lactam carbapenem formulation; and l. aseptically filling the final sterile beta-lactam carbapenem formulation into sterile glass vials, and partially sealing the vials with dry, sterilized, lyophilization stoppers;

m. lyophilizing the formulation by freezing in the glass vials at a temperature of from about −45° to about −40° C. to produce a frozen formulation;

n. primary drying the frozen formulation at a temperature of from about −25° to about −15° C. for about 48 to 60 hours at a pressure of about 80 mTorr;

o. secondary drying the formulation at a temperature of from about 40° to about 60° C. at a pressure of about 80 mTorr or lower for a time period of from about 3 to about 10 hours;

p. cooling the vials to ambient temperature; and q. sealing the vials under a partial vacuum of about 0.9 bar/700 Torr or lower, while maintaining a temperature of about 25° C., wherein the final sterilized beta-lactam carbapenem antibiotic formulation of formula II exhibits a carbapenem concentration of about 200 g/l and a carbonate content of about 1 mole equivalent.

16. The process according to claim 15, wherein the bulk compound to sodium hydroxide solution concentration is 1 mole of bulk compound/ 0.85 moles of sodium hydroxide.

17. The process according to claim 16, wherein the lyophilized solution exhibits a density of about 1.11 g/ml.

18. The process according to claim 17, wherein the step h. temperature, sealing and pressurizing the compounder, is about 2° C.

19. The process according to claim 18, wherein the step e. temperature, dissolving the bulk drug into the sodium bicarbonate solution, is 2° C.

20. The process according to claim 19, wherein step j. temperature, filling the formulation into vials, is from about 0° to about 5° C.

21. The process according to claim 20, wherein the step o. lyophilized, sterile formulation exhibits a density of about 1.11 g/ml at 5° C.

22. The process according to claim 21, wherein the final sterilized beta-lactam carbapenem formulation exhibits a concentration of about 200 g of carbapenem of formula II per liter of total solution.

* * * * *